US00PP21913P3

(12) United States Plant Patent
Ui et al.

(10) Patent No.: US PP21,913 P3
(45) Date of Patent: May 10, 2011

(54) *PETUNIA-CALIBRACHOA* PLANT NAMED 'SAKPXC006'

(50) Latin Name: *Petunia-Calibrachoa hybrida*
Varietal Denomination: SAKPXC006

(75) Inventors: Akinobu Ui, Iwata (JP); Shin Ishikawa, Kakegawa (JP); Niels G. Kristensen, Grauballe (DE)

(73) Assignee: Sakata Seed Company, Yokohama (JP)

( * ) Notice: Subject to any disclaimer, the term of this patent is extended or adjusted under 35 U.S.C. 154(b) by 0 days.

(21) Appl. No.: 12/460,938

(22) Filed: Jul. 27, 2009

(65) Prior Publication Data

US 2011/0023200 P1 Jan. 27, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — Jondle & Associates, P.C.

(57) ABSTRACT

'SAKPXC006' is a new *Petunia-Calibrachoa* hybrid particularly distinguished by having a violet flower color, medium to large flower size and a semi-creeping growth habit.

1 Drawing Sheet

Genus and species: *Petunia-Calibrachoa hybrida.*
Variety denomination: 'SAKPXC006'.

BACKGROUND OF THE INVENTION

The present invention comprises a new and distinct cultivar of *Petunia-Calibrachoa* (Petchoa) referred to by the variety name 'SAKPXC006'. Variety 'SAKPXC006' originated from a selection of a hybridization in Kakegawa, Japan in May of 2003. The male parent of the hybridization was a proprietary hybrid *Calibrachoa* line named '04-62', which had a deep-blue flower color, medium-large flower size and a creeping plant habit. The female parent of the hybridization was a proprietary hybrid *Petunia* line named '04H-64', which had a light purple flower color, medium flower size and mounding plant habit.

In May 2003, the new *Petunia-Calibrachoa* variety was developed using an intergeneric cross between *Petunia hybrida* and a *Calibrachoa hybrida* species. After crossing the parent lines, 1,530 ovules were removed from flowers on the female parent and cultured by standard ovule culture techniques. In December 2003, ten intergeneric hybrid plantlets were transplanted to soilless media for greenhouse culture and acclimatization.

In March 2004, ten plants out of ten hybrid lines were vegetatively propagated to produce rooted cuttings. In April 2004, the ten plants were transplanted to an open field and evaluated for flower color and plant growth habit through July. In July 2004, one plant which had a purple flower color, medium-large size flowers and a semi-creeping plant habit was selected and vegetatively propagated. In January 2007, a naturally-occurring, whole plant mutation line was obtained from the selected plant, which had a violet flower color. From January to October 2007, the new plant was propagated and transplanted. In November 2007, the selection was named 'SAKPXC006' and was found to reproduce true to type in successive generations of asexual propagation.

SUMMARY OF THE INVENTION

The following are the most outstanding and distinguishing characteristics of this new cultivar when grown under normal horticultural practices in Kakegawa, Japan.

1. Violet flower color;
2. Medium to large flower size; and
3. A semi-creeping plant growth habit.

DESCRIPTION OF PHOTOGRAPHS

This new *Petunia-Calibrachoa* plant is illustrated by the accompanying photographs which show the plant's form, foliage and flowers. The photographs are of a plant ten months old grown in Salinas, Calif. in the Spring of 2009. The colors shown are as true as can be reasonably obtained by conventional photographic procedures.

Figure 1:
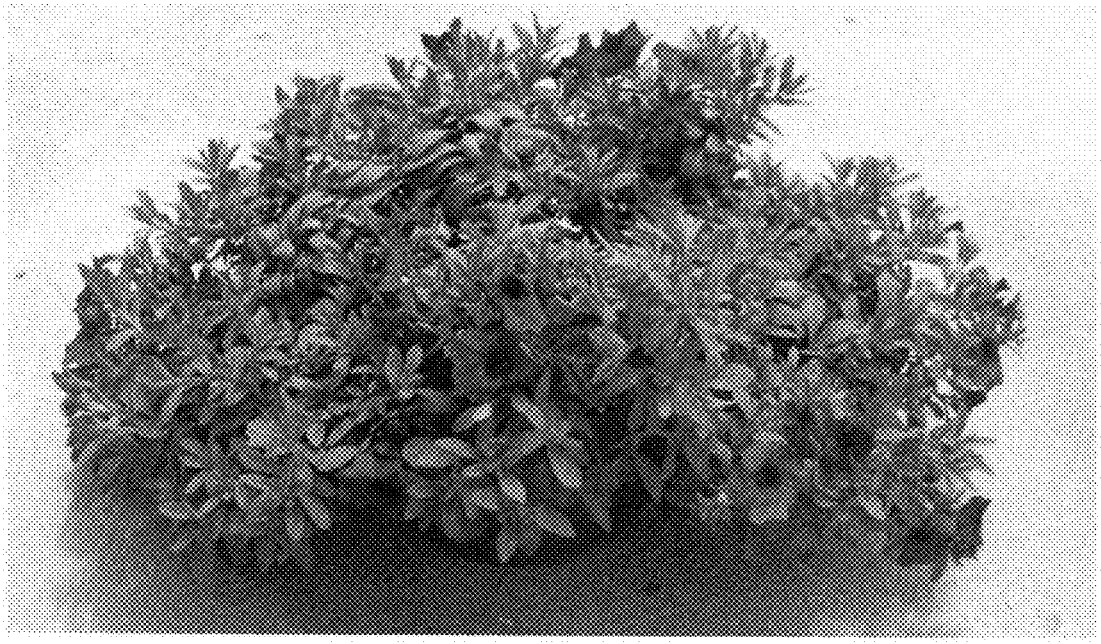

FIG. 1. shows overall plant habit.

Figure 2:
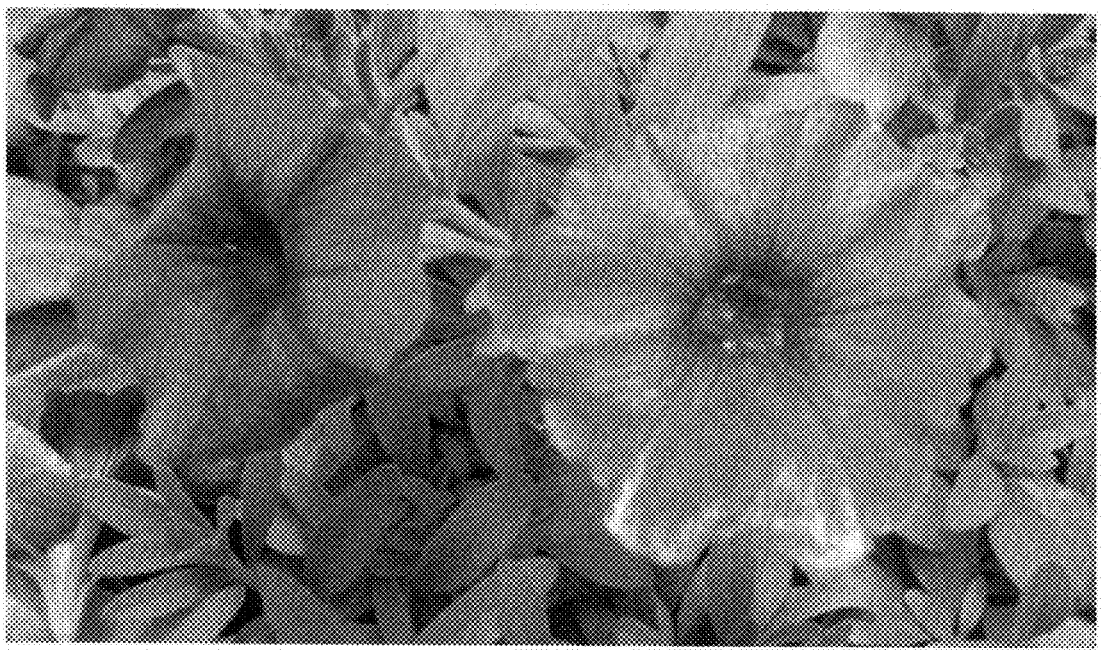

FIG. 2. shows the mature flowers.

DESCRIPTION OF THE NEW CULTIVAR

The following detailed description sets forth the distinctive characteristics of 'SAKPXC006'. The data which define these characteristics were collected from asexual reproductions carried out in Salinas, Calif. The detailed description was taken from plants grown under greenhouse conditions for approximately ten months from transplanting of rooted cuttings. Color references are to the R.H.S. Colour Chart of The Royal Horticultural Society of London (R.H.S.), 4$^{th}$ Edition.

DETAILED BOTANICAL DESCRIPTION

Classification:
- *Family.*—Solanaceae.
- *Species.*—*Petunia-Calibrachoa* intergeneric hybrid.
- *Common name.*—Petchoa.

Parentage:
- *Male.*—Hybrid proprietary *Calibrachoa* plant line '04-62'.
- *Female.*—Hybrid proprietary *Petunia* plant line '04H-64'.

Plant description:
- *Life cycle.*—Tender perennial.
- *Form.*—Decumbent, branching.
- *Habit.*—Semi-creeping.

*Height.*—16.0 cm to 18.0 cm (from soil line to top of foliage).

*Spread.*—60.0 cm to 62.0 cm.

Propagation:

*Type cuttings.*—Vegetative cuttings.

*Time to produce a rooted cutting.*—4 weeks.

*Time to bloom from propagation.*—8 to 10 weeks.

Environmental conditions for plant growth: The terminal 1.0 to 1.5 inches of an actively growing stem was excised. The vegetative cuttings were propagated in four weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. For the first week, the cuttings were misted with water from overhead for 20 seconds, one time per hour. For the second week, the cuttings were misted one time every 2 hours for 10 seconds. After that time, the cuttings were misted occasionally until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:

*Stem color.*—RHS 143B (Green).

*Pubescence.*—Heavy.

*Pubescence color.*—RHS N155A (White).

*Stem description.*—Circular, cross-section.

*Stem diameter.*—0.2 cm.

*Stem length.*—2.0 cm from soil line to first node, 22.0 cm total length.

*Internode length.*—2.0 cm.

Leaves:

*Arrangement.*—Alternate.

*Shape.*—Elliptical.

*Apex.*—Obtuse.

*Base.*—Attenuate.

*Margin.*—Entire.

*Surface.*—Dull.

*Surface pubescence.*—Slight.

*Pubescence color.*—RHS N155A (White).

*Venation.*—Pinnate.

*Venation color.*—Upper surface: RHS 137A (Green). Lower surface: RHS 137B (Green).

*Length.*—4.5 cm.

*Width.*—1.5 cm.

*Color.*—Upper surface: RHS 137A (Green). Lower surface: RHS 137B (Green).

*Fragrance.*—Absent.

Flowers:

*Flowering habit.*—Indeterminate.

*Flower type.*—Solitary.

*Flowering requirements.*—Will flower so long as day length is greater than 12 hours and temperature exceeds 13° C.

*Duration of flowers.*—5 days.

*Corolla.*—5 petals, fused.

*Shape.*—The flowers are funnel shaped with five fissures and a shallow, yet slight, indentation of the petal tip at the midvein.

*Fragrance.*—Absent.

Flower buds:

*Surface.*—Pubescent.

*Length.*—2.7 cm.

*Diameter.*—1.0 cm.

*Shape.*—Ovate.

*Color.*—RHS 79A (Purple) with RHS 79A (Purple) veins.

*Peduncle.*—Length: 3.0 cm. Diameter: 0.15 cm. Color: RHS 143B (Green) with RHS N79A (Purple) toward sepals. Texture: Dull, moderate pubescence. Anthocyanin color: RHS N79A (Purple).

Flower description:

*Flower depth.*—0.5 cm.

*Flower tube length.*—3.0 cm.

*Flower tube diameter.*—1.0 cm.

*Flower diameter.*—5.0 cm.

*Pedicel color.*—RHS 143B (Green) with RHS N79A (Purple).

*Calyx.*—5 sepals, fused below the middle.

*Sepals.*—Shape: Elliptical. Apex: Obtuse. Margin: Entire. Length: 2.0 cm. Diameter: 0.2 cm. Sepal color: Upper surface: RHS 137A (Green). Lower surface: RHS 137B (Green).

*Petal.*—Shape: The flowers are funnel shaped with five fissures and a shallow, yet prominent, indentation of the petal tip at the midvein. Length: 2.0 cm. Apex: Truncate. Margin: Entire. Base: Fused. Pubescence: Glabrous. Lobe length: 2.0 cm. Lobe width: 3.0 cm. Color: Lobe color: Upper surface: Closest to RHS 83B (Violet). Lower surface: RHS 83D (Violet) with RHS N79A (Purple) veins.

*Corolla tube color.*—Inner: RHS 150B (Yellow-green) with RHS N79A (Purple) veins. Outer: RHS 145A (Yellow-green) with N79A (Purple) veins.

*Fragrance.*—Absent.

Reproductive organs:

*Stamen number.*—5, free.

*Stamen color.*—Anther color: RHS 154A (Yellow-green). Filament color: RHS 8A (Yellow).

*Pollen color.*—RHS 6D (Yellow).

*Ovary.*—Superior.

*Placenta arrangement.*—Central.

*Pistil number.*—1 per inflorescence.

*Pistil length.*—1.2 cm.

*Stigma color.*—RHS 145A (Yellow-green).

*Style length.*—1.0 cm.

*Style color.*—RHS 145B (Yellow-green).

Fruit/seed set: No fruit or seeds produced.

Disease and insect resistance: 'SAKPXC006' has excellent resistance to rain, heat and drought. A temperature below 10° C. is not optimal. Plants are susceptible to *Botrytis,* powdery mildew, various stem and root rots, and certain viruses, like Tobacco Mosaic Virus and Impatiens Necrotic Spotted Virus. Plants can be infested with aphids, leafminer, whitefly and various *Lepitopdera.*

COMPARISON WITH PARENTAL LINES AND KNOWN CULTIVARS

'SAKPXC006' is a distinct variety of *Petunia-Calibrachoa* due to its violet flower color and semi-creeping growth habit.

'SAKPXC006' is distinguished from its parents mainly by flower color and plant growth habit as shown in Table 1 below.

TABLE 1

| Characteristic | 'SAKPXC006' | Male Parent: '04-62' | Female Parent: '04H-64' |
|---|---|---|---|
| Flower color | Violet | Deep blue | Light purple |
| Plant growth habit | Semi-creeping | Creeping | Mounding |

'SAKPXC006' is a distinct variety of *Petunia-Calibrachoa* due to its violet flower color and semi-creeping growth habit. 'SAKPXC006' is most similar to the variety 'Kakegawa S90' (U.S. Plant Pat. No. 19,129); however, there are differences in the petal color and plant growth habit as described in the table below (color references are to The Royal Horticultural Society Colour Chart, $4^{th}$ edition):

TABLE 2

| Characteristic | 'SAICPXC006' | 'Kakegawa S90' |
|---|---|---|
| Petal color, upper surface | Closest to RHS 83B (Violet) | RHS N74A (Red-purple) with RHS N77A (Purple) veins |
| Petal color, lower surface | RHS 83D (Violet) with RHS N79A (Purple) veins | RHS N74C (Red-purple) with RHS N77A (Purple) veins |
| Plant growth habit | Semi-creeping | Semi-creeping |

We claim:

1. A new and distinct cultivar of *Petunia-Calibrachoa* hybrid plant as shown and described herein.

* * * * *